United States Patent [19]
Carlin et al.

[11] Patent Number: 5,912,012
[45] Date of Patent: Jun. 15, 1999

[54] EFFERVESCENT SYSTEMS WITH SIMPLIFIED PACKAGING REQUIREMENTS

[76] Inventors: Edward J. Carlin, 794 Fifth St., Secaucus, N.J. 07094; Felix M. Garruto, Jr., 19 King St., Belleville, N.J. 07109

[21] Appl. No.: 08/927,554

[22] Filed: Sep. 6, 1997

[51] Int. Cl.$^6$ ............................. A61K 9/20; A61K 9/46
[52] U.S. Cl. ........................................... 424/464; 424/466
[58] Field of Search .................... 424/464, 466, 424/471, 472

[56] References Cited

U.S. PATENT DOCUMENTS

| | | |
|---|---|---|
| 362,727 | 5/1887 | Divine . |
| 2,297,599 | 9/1942 | Wilen .............................. 167/57 |

*Primary Examiner*—Thurman K. Page
*Assistant Examiner*—Sharon Howard
*Attorney, Agent, or Firm*—Arthur Jacob

[57] ABSTRACT

A three layer effervescent tablet includes a first layer carrying a first effervescent reactant, and a second layer carrying a second effervescent reactant, with the first and second layers, separated by an interposed layer of a material which does not react with either effervescent reactant. This provides an effervescent tablet that does not require any of the special material, handling, or packaging considerations normally needed for effervescent tablets.

14 Claims, 1 Drawing Sheet

EFFERVESCENT SYSTEMS WITH SIMPLIFIED PACKAGING REQUIREMENTS

BACKGROUND—FIELD OF INVENTION

This invention relates to a method of producing effervescent tablets that require no dehumidified production and packaging facilities, and can be packaged in biodegradable or otherwise enviormentally friendly packaging.

BACKGROUND—DESCRIPTION OF PRIOR ART

Products marketed to the consumer in dry form that with the addition of water yield effervescent products have long been known, and their production is currently being practiced widely commercially. This effervescent action is desirable in products for several reasons:

1. It provides a rapid means of tablet disintegration and dissolution.
2. It provides a mechanical action to enhance the action of other ingredients.
3. It provides a pleasing taste sensation to ingestable products.

Effervescent tablets currently in commercial use however, are characterized by a number of objectionable features. The reactive components needed to produce effervescence are physically mingled and compressed into a tablet. This results in a product which in its final form, is extremely moisture sensitive and therefore relatively stable over time. The raw materials must be specially selected for low moisture content. Additionally, the handling and processing at all stages must be done in reduced moisture conditions.

Packaging of these products must also be much more robust than with ordinary tablets, usually involving multi-laminated foil packages designed to ensure air-tightness and provide an absolute moisture barrier.

And so, in addition to higher production and packaging costs, which are ultimately born by the consumer, the whole of civilized humanity is also burdened with an ever increasing amount of effervescent packaging that cannot be recycled and, up until now, cannot be eliminated from the product.

S. R. Divine in U.S. Pat. No. 362,727 discloses an effervescent system made up of two separate masses, each containing one part of the two effervescent reactants, and packaged in a partitioned container. While this approach appears, superficially, to be similar to that proposed by the present invention, it differs in several material respects. In the prior art the two masses must be physically separated by packaging material in order to remain unreactive. Any contact between the two masses in even moderate humidity conditions would cause an effervescent reaction at the interface. Consequently, the integrity of the product is dependent on a partitioned package which is not commercially available, and could not be produced as economically as would a single tablet in a standard strip or blister pack. The alternative of dispensing the masses in separate packages, while producing a viable product, would require twice the packaging material and costs of the proposed invention. Additionally, no matter what the package, the consumer must perform a multi-step operation in order to use the product. The present invention eliminates those multiple steps, as well as the potential for a mixup of the reactants when dispensing several doses of the product at the same time. This last point is a matter of both convenience and expense in preparing food related products, and a much more critical concern when the system is used to dispense medicaments.

F. Wilen, U.S. Pat. No. 2,297,599 discloses an effervescent tablet of multiple parts designed to effervesce vigorously for an appreciable time after the complete liberation of an active substance. The invention consists of a hard inner core of an effervescent mixture surrounded by a soft effervescent shell that also contains actives or flavors. The focus of this product is extended effervescence, and consequently does nothing to alleviate the present packaging or manufacturing conditions which are presently required for effervescent tablets.

E. Fritzberg, et al, U.S. Pat. No. 3,667,962 discloses a rapidly dissolving tablet that is prepared by separating the two effervescent reactants in a pourous, easily friable mass. It is unlike, and considerably more complex, than the proposed invention in that it requires the components to have thermoplastic properties, specific particle size requirements, and the use of both heat and a vacuum to produce a viable product. The term "viable" is used generously, because it is unlikely that highly pourous, easily friable mass would survive the rigors found in the normal distribution of commercial products.

W. Schmitt, U.S. Pat. No. 4,004,036 discloses rapid dissolving effervescent tablets that consist of separating the two reactants by a layer of reacted product at the interface. The product requires a complex procedure involving the injection and extraction of a volatile organic solvent and results in a tablet that has 15–35% voids and would also not be suitable for the rigors of commercial distribution.

D. Whyte, et al, U.S. Pat. No. 4,025,655 describes carbonating a liquid by contact with aluminosilicate molecular sieves saturated with carbon dioxide. This technology has major commercial drawbacks in that it is bulky, expensive, and while providing a source of carbonation, cannot accurately or reliably deliver food flavors or drug compounds in exact amounts. The physical properties of the aluminosilicate material also require protection from atmospheric moisture to prevent premature loss of the adsorbed carbon dioxide.

J. Buchel, U.S. Pat. No. 4,186,215 describes a chamber that separates the effervescent material from the flavor or active constituents, and releases carbon dioxide through the flavor or active and into the liquid poured into the chamber. This requires not only the usual highly protective packaging for the effervescent portion of the product, but a bulky and complex apparatus to allow for delivery of the flavor or active as well.

OBJECTS AND ADVANTAGES

Accordingly, in order to obviate and ameliorate the shortcomings and limitations encountered in the prior art, it is an object of the present invention to present a substantially improved method of manufacturing an effervescent tablet that has no special raw material requirements, and requires no manufacturing conditions which differ from conventional tablets to attain a more stable product.

It is a further object of this invention to produce an effervescent tablet that has none of the expensive and ecologically wasteful packaging requirements that now must be used to store and distribute viable commercial products.

It is still a further objective of this invention to produce an effervescent tablet having all the advantages cited above, and that does not require the consumer to perform complex or multi-step operations to make use of the product.

SUMMARY OF INVENTION

Figure 1:
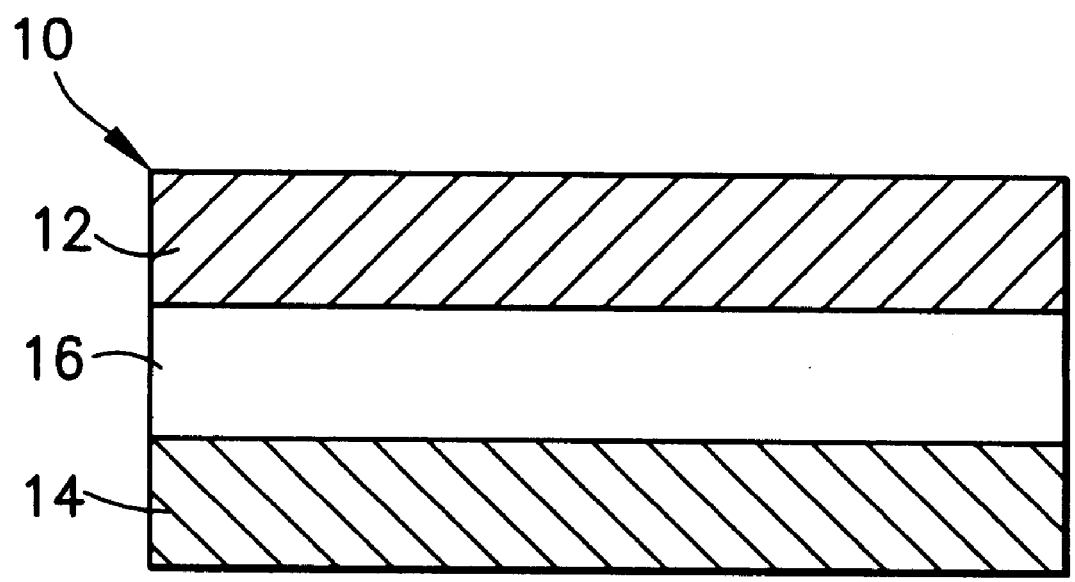
FIG. 1 is a side view showing a tablet of the present invention made in accordance with the method of the present invention and including upper and lower layers containing reactants, separated by a middle layer of inert material.

This invention provides a method of manufacturing an effervescent tablet that does not require any of the special material, handling, or packaging considerations normally required to produce an effervescent tablet. The invention further provides a three layer tablet with reacting components in outer layers, separated by an interposed layer of a material which does not react with the reacting components carried in the outer layers.

DETAILED DESCRIPTION OF THE INVENTION

The invention comprises a multiple-layer tablet, shown in the form of a three layer tablet 10 in which one layer 12 of the outer layers 12 and 14 contains one of the non-aqueous reactants necessary to the effervescent reaction, and the other outer layer 14 contains the other non-aqueous reactant necessary for the effervescent reaction. The two layers 12 and 14 containing the reactants are separated by an interposed layer shown in the form of a middle layer 16 of tablet material that is not chemically involved with the effervescent reaction.

Three layer tablets can be produced using any currently available tabletting technology, or any tabletting technology that may arise in the future, the particular production methods for making three layer tablets not being the object of the present invention.

Each one of the outer layers 12 and 14 of the tablet 10 contains only one of the two reactants necessary to the effervescent reaction. The identity and amount of each of these materials will be determined by the desired composition of the final solution.

The two outer layers 12 and 14 of the tablet 10 must be physically seperated by middle layer 16 which is comprised of one or more materials that are not chemically involved in the effervescent reaction. The thickness of this layer 16 should be, at a minimum, the amount required to achieve and maintain a physical separation of the outer layers 12 and 14 so that tablet 10 remains stable until the tablet 10 is immersed in a liquid.

Any and all other components which may be necessary or desired in the finished product may be divided between any and all the layers of the tablet at the discretion of the formulator, or for the benefit of the finished product.

Other components may include, but are not limited to, binders, lubricants, glidants, disintegrants, wetting agents, sweeteners, colors, flavors, and active ingredients.

The effervescent reactants include and acidic component contained in one of layers 12 and 14, and a basic component contained in the other of the layers 12 and 14. For example, layer 12 includes a carboxylic acid, while layer 14 includes a suitable carbonate or bicarbonate.

Utilizing the above components, tablets 10 can be formulated with carbonated beverage ingredients to produce carbonated beverages, or with dental cleansers, as examples of active ingredients, to produce dental prosthesis cleaners, as well as with other selected components to produce other effervescent products upon immersion in a liquid.

Tableting parameters can be of any size, shape, or hardness that produces a satisfactory product, and are not the object of the present invention.

These tablets 10 can be produced under the same manufacturing conditions as non-effervescent tablets and require no special handling or raw material considerations.

These tablets 10 can then also be blister or strip packaged the same as non-effervescent tablets and require no special packaging materials or techniques.

Summary, Ramifications, And Scope

The present invention then, results in a tablet which employs an effervescent system that renders tablet 10 no more difficult or costly to manufacture and package than a standard commercial tablet, and provides real and unique benefits to the consumer and the ecology. This description should not be construed as limiting the scope of the invention, but as one exemplification thereof. Accordingly, the scope of the invention should be determined by the appended claims and their legal equivalents.

We claim:

1. An effervescent tablet utilizing a multiple-layer effervescent system in which non-aqueous effervescent reactants react with one another in an effervescent reaction, upon immersion of the tablet in a liquid, to form an effervescent product, the tablet comprising:

a first layer containing a first non-aqueous effervescent reactant;

a second layer containing a second non-aqueous effervescent reactant which, in the presence of the liquid, will react with the first non-aqueous effervescent reactant to form the effervescent product; and a third layer of a tablet material containing essentially no constituent which will react with either one of the first and the second effervescent reactants, the third layer being interposed between the first and second layers for separating the first and second effervescent reactants to inhibit effervescent reaction prior to immersion of the tablet in the liquid.

2. The tablet of claim 1 wherein the first effervescent reactant is a carbonate.

3. The tablet of claim 1 wherein the first effervescent reactant is a bicarbonate.

4. The tablet of claim 1 wherein the first effervescent reactant is a carboxylic acid.

5. The tablet of claim 4 wherein the second effervescent reactant is a carbonate.

6. The tablet of claim 4 wherein the second effervescent reactant is a bicarbonate.

7. The tablet of claim 1 wherein the effervescent product is a carbonated beverage and at least one of the first, second and third layers contains a carbonated beverage ingredient.

8. The tablet of claim 1 wherein the effervescent product is a dental prothesis cleaner and at least one of the first, second and third layers contains a dental cleanser.

9. A method of making an effervescent tablet utilizing a multiple-layer effervescent system in which non-aqueous effervescent reactants react with one another in an effervescent reaction, upon immersion of the tablet in a liquid, to form an effervescent product, the method comprising:

providing a first layer containing a first non-aqueous effervescent reactant;

providing a second layer containing a second non-aqueous effervescent reactant which, in the presence of the liquid, will react with the first non-aqueous effervescent reactant to form the effervescent product; and interposing a third layer between the first layer and the second layer, the third layer being of a tablet material containing essentially no constituent which will react with either one of the first and the second effervescent reactants, for separating the first and second effervescent reactants to inhibit effervescent reaction prior to immersion of the tablet in the liquid.

10. The method of claim 9 wherein the first effervescent reactant is a carbonate.

11. The method of claim 9 wherein the first effervescent reactant is a bicarbonate.

12. The method of claim 9 wherein the first effervescent reactant is a carboxylic acid.

13. The method of claim 12 wherein the second effervescent reactant is a carbonate.

14. The method of claim 12 wherein the second effervescent reactant is a bicarbonate.

* * * * *